April 28, 1964 C. FISCHER Plant Pat. 2,395
GLADIOLUS PLANT
Filed April 30, 1963
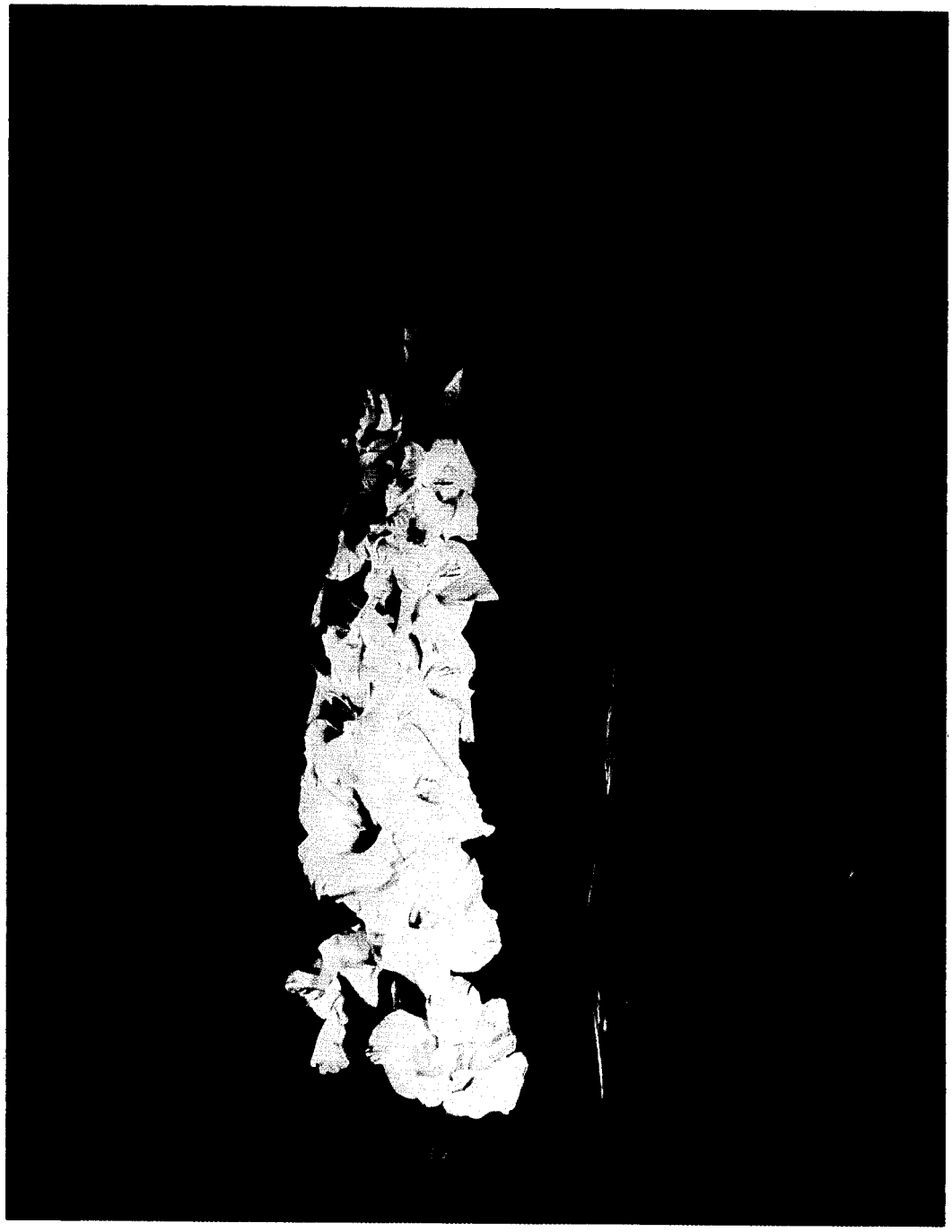
Inventor.
Carl Fischer
By: Robb & Robb
Attorneys United States Patent Office Plant Pat. 2,395
Patented Apr. 28, 1964

2,395
GLADIOLUS PLANT

Carl Fischer, St. Charles, Minn., assignor to Imperial Flowers Limited, Leamington, Ontario, Canada, a corporation of Ontario, Canada Filed Apr. 30, 1963, Ser. No. 277,053
1 Claim. (Cl. Plt.—85)

The present invention relates to a new and distinct variety of gladiolus plant which was originated by me by crossing the variety "Campanile" (unpatented) with the variety "Innocence" (unpatented), the former being the seed parent and the latter being the pollen parent.

As the result of this breeding, I have produced a new and improved gladiolus variety, as evidenced by the following unique combination of characteristics which are outstanding therein and which distinguish it from its parents, as well as from all other varieties of which I am aware:

(1) An extremely vigorous habit of growth;

(2) An ability to grow well in territories ranging widely in latitude and under conditions where the length of the growing day varies widely;

(3) An ability to open well from tight buds; and (4) A distinctive and attractive white general color tonality of the flowers which are creamy white in the half-open stage, but showing a tint of Rose Pink on the inner petals as the flowers age and especially on the lip petals, with a streak of Rose Purple on the reverse of the upper inside petals and in the calyx.

My new variety resembles the variety known as "Christmas White" (plant patent pending) more than any other variety, but differs therefrom particularly by a larger floret size; the habit of its florets facing more nearly upward; less ruffling of the florets and a more creamy white flower color with a tint of Rose Pink as the flowers age.

Asexual reproduction of my new variety by cormels through several generations, as performed by me at St. Charles, Minnesota, shows that the foregoing characteristics and distinctions come true to form and are established and transmitted through succeeding propagations.

The accompanying drawing shows a typical specimen flower spike and typical specimens of the foliage of my new variety, with the flowers in different stages of development ranging from closed buds through partially open buds to fully open flowers, as depicted in color as nearly true as it is reasonably possible to make the same in a color illustration of this character.

The following is a detailed description of my new variety, with color terminology in accordance with the Horticultural Colour Charts issued by the British Colour Council and the Royal Horticultural Society, except where general color terms of ordinary dictionary significance are obvious:

Locality where grown and observed: St. Charles, Minnesota.

Propagation: Holds its distinguishing characteristics through succeeding propagations from cormels.

*Plant*

Growth: Extremely vigorous; prolific propagator.

Blooming habit: Comes into bloom in about 85 days in the case of plantings from large bulbs in Northern latitudes of the United States.

Stems: Erect; strong; very hollow.

*Diameter at base.*—About ½ inch.

*Color (at base).*—Rose-pink.

Foliage: Waxy; straight; leaves range from about 1½ inches to 2 inches wide and attain a height ranging from about 44 inches to 48 inches. Color—deep green.

Disease resistance: Extremely resistant to the usual diseases to which gladiolus varieties are subject, as determined by comparison with other varieties grown in my fields near St. Charles, Minnesota.

Corms (bulbs): Readily produces large corms, and cormlets grow into large corms easily; very plump. Color of flesh—orange-buff in mature corms, but medium yellow in corms formed from bulblets.

*Flower*

Spike: Blossom spike attains height of from 65 inches to 70 inches, with flower head averaging about 30 inches long; bears from 19 to 21 buds, with 9 or 10 buds being open at one time.

Bud:

*Size.*—About 3 inches long when opening.

*Openings.*—Opens well from tight buds; 6 or 7 buds show color at one time.

Flower:

*Arrangement.*—Florets are formally arranged in a double row on the stem.

*Size.*—Individual florets average from about 4¾ inches to 5 inches in diameter, with upper florets being progressively smaller.

*Form.*—Florets are recurved and lightly ruffled and tend to face upward slightly on some spikes.

*Keeping qualities.*—Keeps well.

Petals:

*Shape.*—Round; recurved; slightly ruffled.

*Size.*—Upper petals—about 2½ inches wide. Lip petal—about 1½ inches wide.

*Aspect.*—Leathery substance.

*Fragrance.*—None.

*Color.*—White, with half-open flowers being creamy white; as the flowers age, they show a tint of Rose Pink, Plate 427/2 on the inner petals, and especially on the lip petals, with a streak of Rose Purple, Plate 553/1 on the reverse of the upper inside petals and in the calyx.

*Reproductive Organs*

Stamens: Color—Rose Purple, Plate 533.

Pistil: Color—white.

I claim:

A new and distinct variety of gladiolus plant, substantially as herein shown and described, characterized particularly as to novelty by the unique combination of an extremely vigorous habit of growth, an ability to grow well in areas extending over a wide range of latitude and under growing day conditions of widely varying length, an ability of the flowers to open well from tight buds, and a distinctive and attractive white general color tonality of the flowers, said flowers being creamy white in the half-open stage but showing a tint of Rose Pink on the inner petals as the flowers age, and especially on the lip petals, with a streak of Rose Purple on the reverse of the upper inside petals and in the calyx.

No references cited.